United States Patent [19]
Inaba et al.

[11] Patent Number: 5,264,085
[45] Date of Patent: Nov. 23, 1993

[54] METHOD OF SEPARATING COMPONENTS OF PHENOLS MIXTURE BY DISTILLATION

[75] Inventors: Masashi Inaba; Yoshikazu Higaki; Kimikatsu Jinno; Mitsugi Kataoka; Norio Sato; Masayuki Honda, all of Yokkaichi, Japan

[73] Assignee: Mitsubishi Petrochemical Company, Ltd., Tokyo, Japan

[21] Appl. No.: 932,586

[22] Filed: Aug. 20, 1992

[30] Foreign Application Priority Data

Aug. 28, 1991 [JP] Japan .................................. 3-217223
Apr. 22, 1992 [JP] Japan .................................. 4-103117

[51] Int. Cl.$^5$ .................... B01D 3/00; C07C 37/72; C07C 37/74; C07C 39/07
[52] U.S. Cl. .................................. 203/39; 203/43; 203/96; 203/97; 203/98; 203/93; 203/94; 203/99; 203/DIG. 19; 203/DIG. 23; 568/749; 568/916; 568/918
[58] Field of Search .................... 203/39, 99, DIG. 19, 203/DIG. 23, 43, 96, 97, 98, 93, 94; 568/749, 750, 913, 916, 918

[56] References Cited

U.S. PATENT DOCUMENTS 4,328,377 5/1982 Mori et al. .......................... 568/798
4,744,869 5/1988 Saito et al. .................. 203/DIG. 23
4,832,796 5/1989 Fulmer .................................. 203/29

FOREIGN PATENT DOCUMENTS 0028910 5/1981 European Pat. Off. .
0332615 9/1989 European Pat. Off. .
0753475 7/1956 United Kingdom .

OTHER PUBLICATIONS

Patent Abstracts of Japan, vol. 5, No. 106 (C-62)(778), Jul. 10, 1981, & JP-A-56 46 829, Apr. 28, 1981, Mitsuo Onobusa, et al., "Separation of Methylphenol".
Chemical Abstracts, vol. 101, No. 14, Oct. 1, 1984, & Abstract No. 112775s, Jun. 6, 1984, pp. 98, "Separation of Anisole".

*Primary Examiner*—Virginia Manoharan
*Attorney, Agent, or Firm*—Oblon, Spivak, McClelland, Maier & Neustadt

[57] ABSTRACT

A method of continuously distilling off the components of a mixture containing phenols, water and methanol using a single distillation column, wherein methanol is recovered from the top of the column, water containing phenols is dragged as a side stream from a recovery section of the column, and phenols are recovered as a bottom product. The method permits efficient separation by the single distillation column of the three components with high purity and low utility energy.

11 Claims, No Drawings

METHOD OF SEPARATING COMPONENTS OF PHENOLS MIXTURE BY DISTILLATION

BACKGROUND OF THE INVENTION

The present invention relates to a method of continuously separating a mixture which contains phenols, water and methanol into three separate effluent streams using a single distillation column.

Generally known methods of separating each component from a mixture containing phenols, water and methanol include the following:

(1) A method comprising distilling off water and methanol from the top of a first distillation column and recovering phenols from the bottom of the column, and then separating water from methanol by a second distillation column (Japanese Patent Laid-open No. 63-188636, etc); and (2) A method comprising separating methanol by distillation and then separating the phenols and water by liquid-liquid phase separation.

However, method (1) has problems in that at least two distillation columns are required, and in that since water is distilled off from the top of the first column, a great deal of energy is required for evaporating the water.

The method (2) has a problem in that the phenols separated must be dehydrated since the phenols stream obtained by two-phase separation contains large quantities of water because water is highly soluble in phenols.

On the other hand, a continuous distillation method with side-stream drag, which is termed a "side cut method", is employed in the field of petroleum refining and for separating small quantities of impurities, high-purity fractions and the like. However, there are extremely few cases of this method being employed for mixtures containing phenols, methanol, water and the like. A known case using this method is only one in which a mixture containing four components including anisole, methanol, water and phenols is distilled, and a side-stream containing methanol/water and anisole is dragged from the enriching section of the distillation column, and then subjected to oil/water phase separation to obtain anisole (Japanese Patent Publication No. 3-20373).

SUMMARY OF THE INVENTION

It is an object of the present invention to provide a method of efficiently separating three components of a mixture containing phenols, methanol and water by distillation using a single distillation column.

The present invention provides a method of continuously separating components of a hydrous phenols mixture containing methanol by distillation which comprises recovering methanol from a top of a single distillation column, dragging water containing phenols as a side stream from the recovery section of the distillation column and the dehydrated phenols as a bottom product.

DETAILED DESCRIPTION OF THE INVENTION

A phenols mixture supplied to the distillation column by the method of the present invention contains phenols, water and methanol, and moreover it may contain small quantities of other components within a range which has no effect on the object distillation separation.

Examples of phenols include phenol, alkylphenols such as cresol, dimethylphenol and the like.

The composition of the phenol mixture preferably consists of 10 to 65% by weight phenols, 30 to 60% by weight methanol and 5 to 30% by weight water. Particularly, the ratio by weight of water to phenols is preferably at least 0.1.

An example of such a mixture is the reaction solution obtained after methylation in the process of producing methylated phenols such as cresol, xylenol and the like by reaction of phenol and/or ortho-cresol with methanol.

The distillation column used in the method of the present invention may be either a packed column or a plate column. Although the total number of theoretical plates depends upon the desired degree of separation, the number must be about 10 to 35 as a standard.

The position of the feed stage for supplying the hydrous phenols mixture is not particularly limited, and it is generally preferably near the central portion of the distillation column.

In the method of the present invention, it is very important that the side cut stage of dragging water containing the phenols is placed in the recovery section of the distillation column below the supply stage. This is because if water is dragged by side cut from the enriching section above the feed stage, it would be difficult to avoid having the methanol enter the water side stream.

In the present invention, the side cut stage is placed in the recovery section of the distillation column below the position where a solution to be treated is supplied, thereby efficiently separating and purifying the three components of a phenols mixture containing phenols, methanol and water using the single distillation column.

The required number of theoretical plates in the enriching section of the distillation column is about 5 to 30, preferably 10 to 20. The recovery section should have 3 to 20 plates, preferably 5 to 15 plates, from the supplying plate to the side cut plate, and 2 to 10 plates, preferably 2 to 7 plates, from the side cut plate to the bottom of the column.

Although the distillation temperature depends upon the distillation pressure, the temperatures of the top and the bottom of the column are 50° to 60° C. and 180° to 190° C., respectively, at atmospheric pressure.

Although the distillation is generally performed at atmospheric pressure, it may be performed at increased pressure or reduced pressure according to demand.

Although the separation efficiency representing the performance of the column depends upon the operating conditions and design of the column and the like, methanol having a purity of at least 95% can be recovered from the top of the column. An increase in the number of plates in the enriching section enables the recovery of methanol having a purity of at least 99% and a water content of less than 1000 ppm. It is disadvantageous in view of energy to increase the water content of the methanol distilled off from the top of the column because the amount of water evaporated from the phenol mixture to be distilled is increased.

The side cut stream which contains mainly water may be either in a vapor phase or a liquid phase. However, from the view point of energy consumption, it is preferable to drag the water side stream in a liquid phase to conserve large amounts of water evaporation heat.

When the water side stream is dragged in a liquid phase using a packed column, any type of liquid holding device (e.g. chimney tray) can be used.

Even though the side cut stream contains mainly water, it also generally contains about 5 to 50% by weight phenols and is thus subjected to liquid-liquid phase separation of water and phenols by decantation.

The decantation temperature should preferably be 60° C. or less, most preferably about 40° C., because of the differences in density of the two liquid phases, in the solubility of phenols and water, and in the freezing points of the phenols.

Since some water dissolves in the phenols layer obtained by liquid-liquid separation, the phenols layer is preferably refluxed to a position near the side stream stage.

On the other hand, the phenols dissolve in the water layer obtained by liquid-liquid separation, and the concentration of the phenols depends upon the temperature of liquid-liquid separation and the composition of the phenols. For example, when the hydrous phenols mixture supplied results from methylation of phenol, and when the decanter temperature is about 40° C., about 2 to 3% by weight of phenols dissolve in the water layer obtained by liquid-liquid separation. Usually this water layer stream is treated by solvent extraction or adsorption to recover phenols before disposal.

The methanol content in the water layer obtained by liquid-liquid separation must be as low as possible from the viewpoint of the problems with respect to methanol loss and waste water treatment. However, the method of the present invention is capable of decreasing the methanol content to about 0.5% or less. If the methanol content in the side stream is increased, not only is liquid-liquid separation of water and phenols in the decanter section not sufficiently effected, but also a high methanol content adversely affects the recovery of the phenols dissolving in the water layer by adsorption, extraction or the like. There is also the problem that methanol leaks into the final waste water treated by adsorption, extraction or the like and increases the BOD value in the final waste water.

The water layer obtained by liquid-liquid separation using the decanter can also be used as water to be supplied to the distillation column described below and reused as a raw material for methylation as is because it contains small amounts of phenols.

Phenols containing substantially no methanol or water can be continuously recovered as the bottom product from the distillation column. The water content of the bottom product can be decreased to 2000 ppm or less.

In the side-cut type continuous distillation column of the present invention, the ratio of water to phenols in the phenol mixture supplied is important. It is necessary that water sufficiently prevails in a portion near the side cut plate in the distillation column. However, when the ratio of water to phenols is low, water does not tend to have sufficient content in the portion below the side cut stage, thereby causing unstable temperature distributions in the portion near the side cut stage and thus making the distillation column unstable.

The ratio of water to phenols should thus be at least 10% by weight, preferably 10 to 70% by weight. When the ratio of water to phenols is less than 10% by weight (water/phenols 0.1), the stable distillation operation can be maintained by additionally supplying water to the distillation column. Water is preferably supplied to the recovery section below the side cut stage. At this time, the water obtained by liquid-liquid separation using the decanter provided outside the distillation column may be used.

When water is supplied from the outside of the distillation column, e.g., from the decanter or the like, if the ratio α of water supplied is defined as follows:

$$\alpha = \frac{\text{amount of water supplied to distillation column}}{\text{amount of water dragged to outside}}$$

the α value is preferably within the range of about 0.05 to 0.5.

The distillation column may be designed so that water can be supplied to the portion below the side cut stage using an internal decanter in the distillation column. By using a chimney tray, for example, as such internal decanter installation is facilitated, and liquid-liquid separation of phenols and water is effected in the section. The water layer obtained is partially supplied to the portion below the side cut stage, whereby internal reflux of water can be achieved. Water can also be refluxed to (he portion below the side cut stage by the overflow from the tray section.

A system for supplying heat to the distillation column may be a system in which a reboiler is provided at the bottom of the column or a system in which a reboiler is further provided on the side cut stage so that heat can be supplied in two stages.

When the side reboiler is installed, it is preferably installed in the same position as the side cut stage or a position several plates above the side cut stage.

Since the water concentrations near the side cut stage and near the stage where the side reboiler is installed in the distillation column are high, and since the temperature is about 100° C. at atmospheric pressure, when the side reboiler is installed, low-pressure steam or the like can be used as a heat source for the reboiler. Although part of the side cut stream and any other stream dragged from the stage near the side cut can also be used to feed to the side reboiler, the method of partially introducing the side cut stream to the side reboiler is simple and preferable. A conventional type of reboiler such as a thermosiphon reboiler, a forced circulation reboiler or the like can be used as the side reboiler.

Although the ratio of the quantity of heat supplied from the side reboiler to the quantity of heat supplied from the bottom reboiler at the bottom of the column depends upon the composition of the phenols mixture supplied to the distillation column, the ratio is about 3:1 to 1:1. The ratio of the side reboiler using a low-temperature heat source is preferably high because the energy cost is decreased.

The method of the present invention requires no complicated operation and is capable of separating the three components, i.e., methanol, water and phenols, with high purity at the same time and decreasing the energy cost. The method of the present invention can thus be very useful in the industrial field.

EXAMPLES

The present invention is described in detail below with reference to the examples.

In the examples, percentages refer to percentages by weight.

Phenols and methanol were analyzed by gas chromatography using a hydrogen flame detector, and water was analyzed by a Karl Fischer moisture meter.

Examples 1 to 3

A packed column having an inner diameter of 40 mm and a number of 26 theoretical stages was used as a distillation column. A hydrous phenols mixture having the composition below was supplied to a position 13 stages from the top of the column, and a side cut stream was dragged from the 22nd stage position so that the feed solution was continuously distilled and separated into three effluent streams from the top, the bottom and the side stream.

Distillation was effected at atmospheric pressure, and the supply speed of the hydrous phenols mixture and the reflux ratio were as shown in Table 1.

A chimney tray was provided at the side cut stage in the distillation column so that the solution was partially dragged to the outside of the column, the remainder being caused to overflow. Since the overflowing liquid from the chimney tray contained water, reflux of water occurred in the distillation column.

The side stream solution dragged from the side cut stage was subjected to liquid-liquid separation by cooling at 40° C. using a decanter. The water layer obtained was partially exhausted as waste water, and both the remaining water layer and the phenol layer were supplied to the portion below the side cut stage. At this time, the ratio α of water supplied was about 1.5. The results are shown in Table 1.

| Hydrous phenols mixture: | |
|---|---|
| Methanol | 45.5% |
| Water | 12.0% |
| Phenol | 1.9% |
| Ortho-cresol | 13.0% |
| 2,6-xylenol | 27.5% |

TABLE 1

| | Example 1 | Example 2 | Example 3 |
|---|---|---|---|
| Feed rate (g/hr) | 300 | 310 | 540 |
| Reflux ratio | 2.0 | 0.75 | 0.75 |
| Top product: | | | |
| Methanol purity (%) | 99.8< | 99.8< | 99.7< |
| Water concentration (ppm) | 347 | 737 | 1810 |
| Water layer obtained by liquid-liquid separation of side stream: | | | |
| Methanol concentration (ppm) | 181 | 140 | 223 |
| Phenols concentration (%) | 2.5 | 2.1 | 2.0 |
| Bottom product: | | | |
| Methanol concentration (ppm) | 276 | 100> | 100> |
| Water concentration (ppm) | 1043 | 680 | 904 |
| Phenols concentration (%) | 99.5< | 99.5< | 99.5< |

Example 4

The hydrous phenols mixture below was used, and the components thereof were separated by distillation by the same method as that employed in Example 1 excepting that the reflux ratio was 1, and the feed rate was 300 cc/hr. At this time, the water supply ratio c was about 4.

As a result the top product showed a methanol purity of 99.84% and a water concentration of 720 ppm, the water layer obtained by two-layer separation using a decanter showed a methanol concentration of 310 ppm and a phenols concentration of 2.5%, and the bottom product showed a water concentration of 700 ppm and no detection of methanol.

| Hydrous phenols mixture: | |
|---|---|
| Methanol | 52.1% |
| Water | 3.6% |
| Phenol | 2.0% |
| Ortho-cresol | 14.2% |
| 2,6-xylenol | 28.1% |

Examples 5 to 7

A packed column having an inner diameter of 40 mm and 26 theoretical stages was used as a distillation column. A hydrous phenols mixture having the composition below was heated to 80° C. and was supplied to a position 13 stages from the top of the column and a side cut stream was dragged from the 22nd stage position so that the feed solution was continuously distilled off from the top, the bottom and the side stream. Distillation was effected at atmospheric pressure, and the reflux ratios were as shown in Table 2.

A side reboiler was connected to the side cut chimney trap, and the liquid on the chimney trap was partially dragged to the outside of the column, the remainder being caused to overflow in the column. Since the overflowing solution contained water, reflux of water occurred in the distillation column.

The side stream solution dragged from the side cut stage was subjected to liquid-liquid separation by cooling at 40° C. using a decanter. The entire phenol layer obtained was recycled to the portion below the side cut stage. The water layer was exhausted as waste water in an amount corresponding to the amount of the raw material supplied, the remainder being recycled to the portion below the side cut stage and the side reboiler.

At this time, the ratio a of water supplied was about 1.5. The results are shown in Table 2.

| Hydrous phenols mixture: | |
|---|---|
| Methanol | 45.8% |
| Water | 11.8% |
| Phenol | 1.9% |
| Ortho-cresol | 12.0% |
| 2,6-xylenol | 27.5% |

TABLE 2

| | Example 5 | Example 6 | Example 7 |
|---|---|---|---|
| Reflux ratio | 1.0 | 0.8 | 1.0 |
| Top product: | | | |
| Methanol purity (%) | 99.88 | 97.77 | 99.92 |
| Water concentration (ppm) | 1200 | 2230 | 800 |
| Water layer obtained by liquid-liquid separation of side stream: | | | |
| Methanol concentration (ppm) | 140 | 80 | 130 |
| Phenols concentration (%) | 2.10 | 2.74 | 2.31 |
| Bottom product: | | | |
| Methanol concentration (ppm) | — | — | — |
| Water concentration (ppm) | 30 | 10 | 30 |
| Phenols concentration (%) | >99.9 | >99.9 | >99.9 |
| Quantity of heat (kcal/hr): | | | |
| Side reboiler | 58.7 | 48.7 | — |
| Bottom reboiler | 25.9 | 27.2 | 85.2 |

What is claimed is:

1. A method of continuously separating components of a phenols mixture containing water and methanol obtained by methylation reaction of phenols, the ratio of water to phenols being at least 10% by weight, which comprises supplying said phenols mixture into a single distillation column, recovering methanol from the top of said single distillation column, dragging water containing phenols as a side cut stream from a side cut stage located at a recovery section of said distillation column below the position where said phenols mixture is supplied, subjecting said side cut stream to liquid-liquid separation to obtain a phenol layer, introducing said phenol layer to said distillation column, and recovering dehydrated phenols as a bottom product of said single distillation column.

2. A method according to claim 1, wherein said phenols mixture contains 10 to 65% weight phenols, 30 to 60% by weight methanol and 5 to 30% by weight water.

3. A method according to claim 1, wherein said phenols mixture is supplied to a portion near the center of said distillation column.

4. A method according to claim 1, wherein the water side cut stream containing phenols is a liquid phase.

5. A method according to claim 1, wherein a side reboiler is provided as a heat source for said distillation column.

6. A method according to claim 1, wherein said phenols consist of a mixture of phenol and alkylphenols as main components.

7. A method according to claim 6, wherein said alkylphenols consist of a mixture of cresol and dimethylphenol.

8. A method of continuously separating by distillation components of a phenols mixture containing water and methanol obtained by methylation reaction of phenols, which comprises supplying said phenols mixtures into a single distillation column, recovering methanol from the top of said distillation column, dragging water containing phenols as a side cut stream from a side cut stage located at a recovery section of said distillation column below the position where said phenols mixture is supplied subjecting said side cut stream to liquid-liquid separation to obtain a phenol layer, supplying additional water to a phenol layer obtained by liquid-liquid separation of the side cut stream to said distillation column, and recovering dehydrated phenols as a bottom of said distillation column.

9. A method according to claim 8, wherein said additional water is part of water separated from said side cut stream by liquid-liquid separation.

10. A method according to claim 9, wherein the ratio of an amount of said additional water to that of water dragged to outside is within the range of about 0.05 to 0.5.

11. A method according to claim 8, wherein said additional water is supplied as internal reflux by overflow from the side cut stage of the distillation column.

* * * * *